(12) United States Patent
Sung et al.

(10) Patent No.: US 8,324,898 B2
(45) Date of Patent: Dec. 4, 2012

(54) TAILORED RADIOFREQUENCY PULSES FOR UNIFORM SATURATION IN MAGNETIC RESONANCE IMAGING

(75) Inventors: Kyunghyun Sung, Union City, CA (US); Krishna S. Nayak, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 544 days.

(21) Appl. No.: 12/619,300

(22) Filed: Nov. 16, 2009

(65) Prior Publication Data

US 2010/0127703 A1 May 27, 2010

Related U.S. Application Data

(60) Provisional application No. 61/114,527, filed on Nov. 14, 2008.

(51) Int. Cl.
*G01V 3/00* (2006.01)
(52) U.S. Cl. ........................................ 324/309; 324/307
(58) Field of Classification Search .................. 324/309, 324/307, 314, 300
See application file for complete search history.

(56) References Cited

U.S. PATENT DOCUMENTS

| | | | | |
|---|---|---|---|---|
| 4,782,839 A | * | 11/1988 | Hennig et al. | 600/413 |
| 4,881,032 A | * | 11/1989 | Bottomley et al. | 324/309 |
| 5,019,784 A | * | 5/1991 | Garwood et al. | 324/307 |
| 6,320,377 B1 | | 11/2001 | Miyazaki et al. | |
| 6,995,559 B2 | | 2/2006 | Agilandam et al. | |
| 7,446,526 B2 | * | 11/2008 | Cunningham et al. | 324/307 |
| 2005/0093541 A1 | | 5/2005 | Agilandam et al. | |

FOREIGN PATENT DOCUMENTS

| | | |
|---|---|---|
| JP | 07313484 A1 | 5/1995 |
| WO | 03093855 A1 | 11/2003 |

OTHER PUBLICATIONS

PCT Application No. PCT/US2009/064588, filed Nov. 16, 2009, International Search Report and Written Opinion of the International Searching Authority (KIPO), mailed Jun. 22, 2010.
Atkinson, D. J. et al. First-Pass Cardiac Perfusion: Evaluation with Ultrafast MR Imaging. Radiology, 174(3):757-762, Mar. 1990.
Cunningham, C. H. et al. Saturated Double Angle Method for Rapid B1+ Mapping. Magnetic Resonance in Medicine, 55:1326-1333, 2006.

(Continued)

*Primary Examiner* — Louis Arana
(74) *Attorney, Agent, or Firm* — McDermott Will & Emery LLP

(57) ABSTRACT

Embodiments of the present disclosure are directed to systems and methods for providing tailored RF pulse trains, based on estimated B0 and B1 profiles, for uniform saturation for MRI techniques. The tailored pulse trains are optimized to minimize residual longitudinal magnetization in target tissue. The B0 and B1 profiles can be measured a priori over a desired region of a patient, e.g., the heart, and can overcome or mitigate SAR and B1 inhomogeneity constraints. In exemplary embodiments, the tailored pulse trains can include hard pulses with unequal weighting. In other embodiments, the tailored pulse trains can include BIR-4 pulse trains that are optimized to minimize residual longitudinal magnetization in target tissue. The tailored pulse train designs can improve the immunity to B1 variation while maintaining low RF power. MRI systems, methods, and controllers for providing tailored pulse trains are described.

26 Claims, 8 Drawing Sheets
(3 of 8 Drawing Sheet(s) Filed in Color)

OTHER PUBLICATIONS

Edelman, R. R. et al. Gadolinium-Enhanced Off-Resonance Contrast Angiography. Magnetic Resonance in Medicine 57(3):475-484, 2007.

Ferreira, P. et al. Investigating Myocardial Field Distortions During First Pass of a Gadolinium based Contrast Agent in Perfusion Studies. Proc. Intl. Soc. Mag. Reson. Med. 16, p. 46, Toronto, 2008.

Kellman, P. et al. Imaging Sequences for First Pass Perfusion—A Review. Journal of Cardiovascular Magnetic Resonance, 9(3):525-537, 2007.

Kim, D. et al. B0 and B1-Insensitive Uniform T1-Weighting for Quantitative, First-Pass Myocardial Perfusion Magnetic Resonance Imaging. Magnetic Resonance in Medicine 54(6):1423-1429, 2005.

Kim, D. et al. Comparison of the Effectiveness of Saturation Pulses in the Heart at 3T. Magnetic Resonance Medicine 59(1):209-215, 2008.

Kino, A. et al. Comparison of different field insensitive saturation pulses for 3T cardiac first pass perfusion. Proc. Intl. Mag. Reson. Med. 15 (2007), p. 2532.

McNamara, M. T. et al. Acute Myocardial Ischemia: Magnetic Resonance Contrast Enhancement with Gadolinium-DTPA. Radiology, 1984, 153(1):157-163.

Noeske, R. et al. Human Cardiac Imaging at 3 T Using Phased Array Coils, Magnetic Resonance in Medicine 44:978-982 (2000).

Oesingmann, N. et al. Improved Saturation RF Pulse Design for Myocardial First-Pass Perfusion at 3T. Journal of Cardiovascular Magnetic Resonance, 6(1):373-374, 2004.

Ogg, R. J. et al. Wet, a T1- and B1—Insensitive Water-Suppression Method for in Vivo Localized 1 H NMR Spectroscopy. Journal of Magnetic Resonance, Series B, 104(1):1-10, 1994.

Schwitter, J. et al. MR-IMPACT: comparison of perfusion-cardiac magnetic resonance with single-photon emission computed tomography for the detection of coronary artery disease in a multicentre, multivendor, randomized trial. European Heart Journal (2008) 29(4):480-489, 2008.

Staewen, R. S., et al. 3-D FLASH Imaging Using a Single Surface Coil and a New Adiabatic Pulse, BIR-4. Investigative Radiology, 25:559-567 (1990).

Sung, K. et al. Design and Use of Tailored Hard-Pulse Trains for Uniformed Saturation of Myocardium at 3 Tesla. Magnetic Resonance in Medicine 60:997-1002 (2008).

Sung, K. et al. Measurement and Characterization of RF Nonuniformity Over the Heart at 3T Using Body Coil Transmission. Journal of Magnetic Resonance Imaging, 27(3):643-648, 2008.

* cited by examiner

FIG. 3    300

Table 1
Prescribed Flip Angles, Max [$M_z/M_0$], and Relative RF Power for Optimized Tailored Pulse Trains

| n | Optimal weighting | | | | | | Max [$M_z/M_0$] | Relative RF power[a] |
|---|---|---|---|---|---|---|---|---|
| 1 | 114° | | | | | | 0.737 | 1.3 |
| 2 | 116° | 231° | | | | | 0.268 | 3.9 |
| 3 | 96° | 228° | 141° | | | | 0.087 | 5.2 |
| 4 | 120° | 90° | 180° | 230° | | | 0.043 | 6.9 |
| 5 | 90° | 110° | 145° | 205° | 235° | | 0.016 | 8.7 |
| 6 | 90° | 170° | 130° | 105° | 220° | 240° | 0.007 | 10.6 |

[a] Relative RF energy is defined as the pulse RF energy divided by the RF energy of a single 90° hard pulse (duration 0.5 ms). All pulses use a peak B1 amplitude of 0.115G.

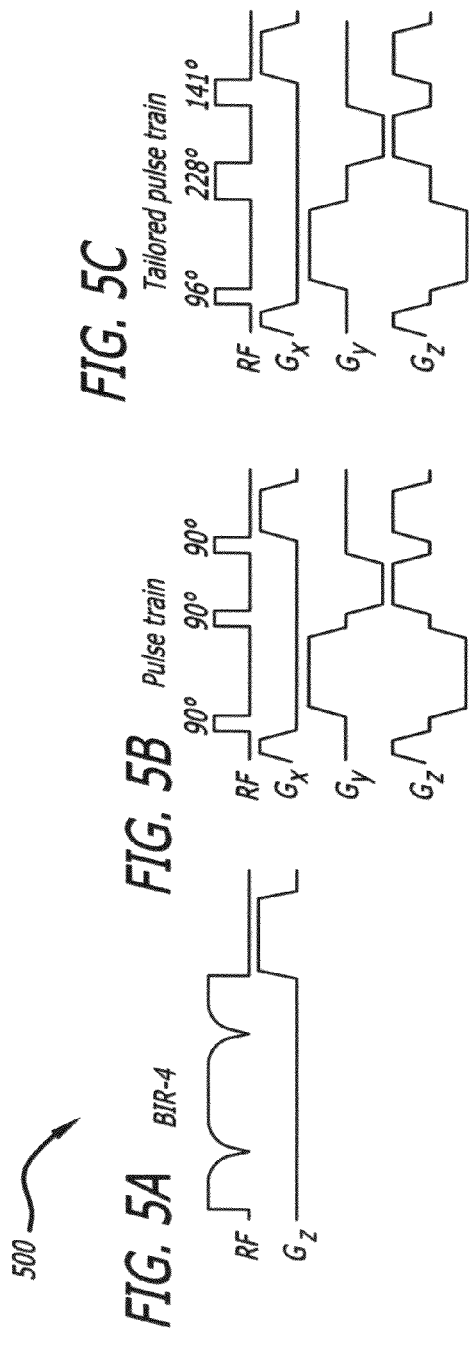
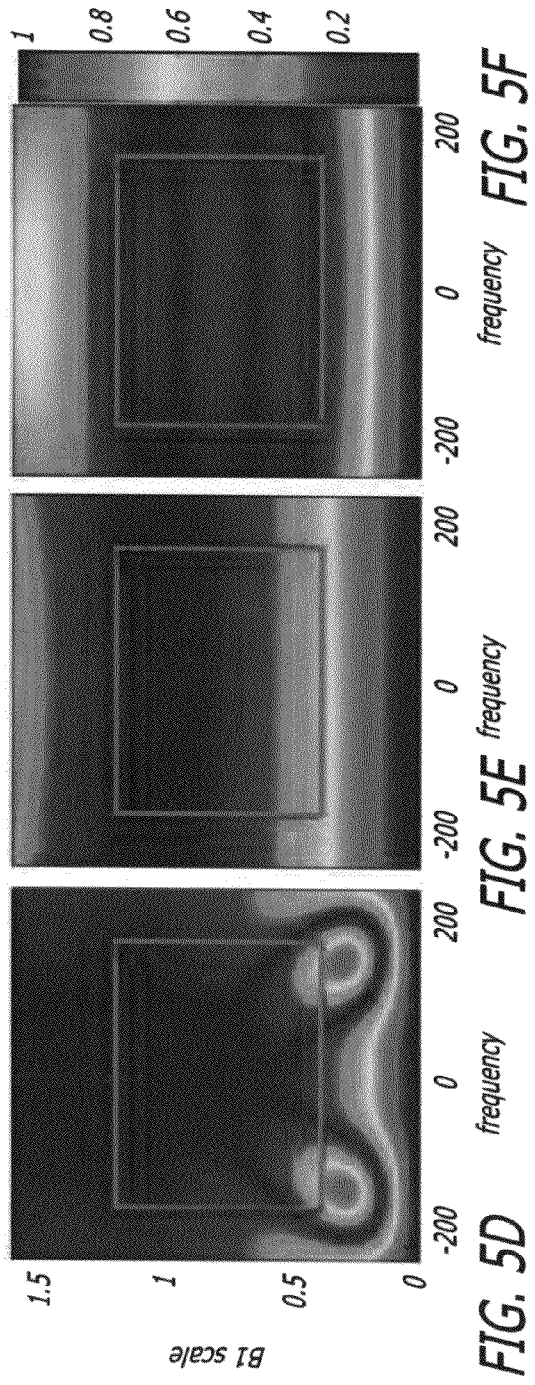

FIG. 7
Table 2
In Vivo Performance of Myocardial Saturation Pulses at 3 Tesla
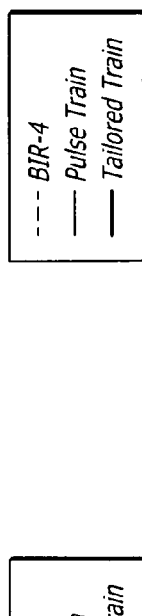
| | RF Pulse duration | Relative RF power | LV | | LV and RV | |
|---|---|---|---|---|---|---|
| | | | Max[$M_z/M_0$] | Mean[$M_z/M_0$] | Max[$M_z/M_0$] | Mean[$M_z/M_0$] |
| BIR-4 | 8.0 msec | 21.6 | 0.28 ± 0.066 | 0.11 ± 0.022 | 0.57 ± 0.259 | 0.14 ± 0.046 |
| Conventional pulse train | 6.5 msec | 3 | 0.32 ± 0.133 | 0.12 ± 0.055 | 0.81 ± 0.335 | 0.21 ± 0.093 |
| Tailored pulse train | 7.7 msec | 5.2 | 0.22 ± 0.062 | 0.09 ± 0.017 | 0.26 ± 0.086 | 0.097 ± 0.019 |
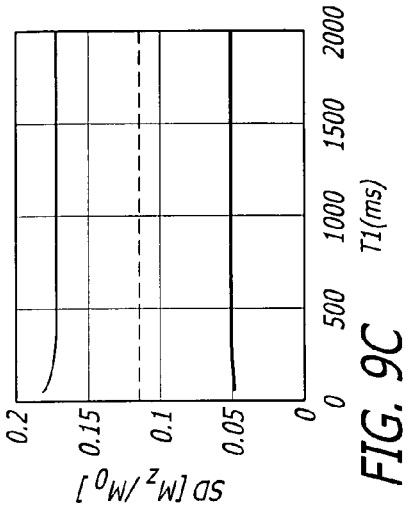
FIG. 9C
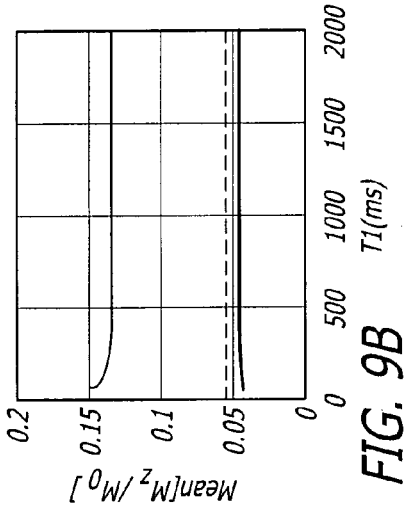
FIG. 9B
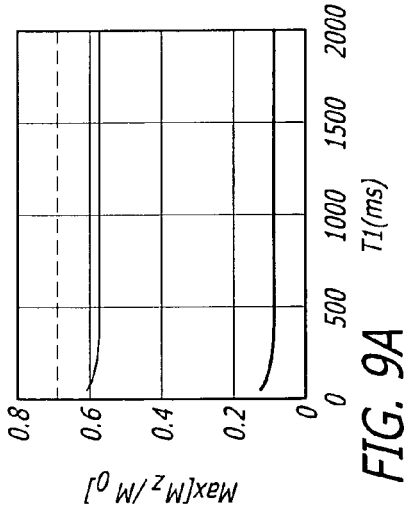
FIG. 9A

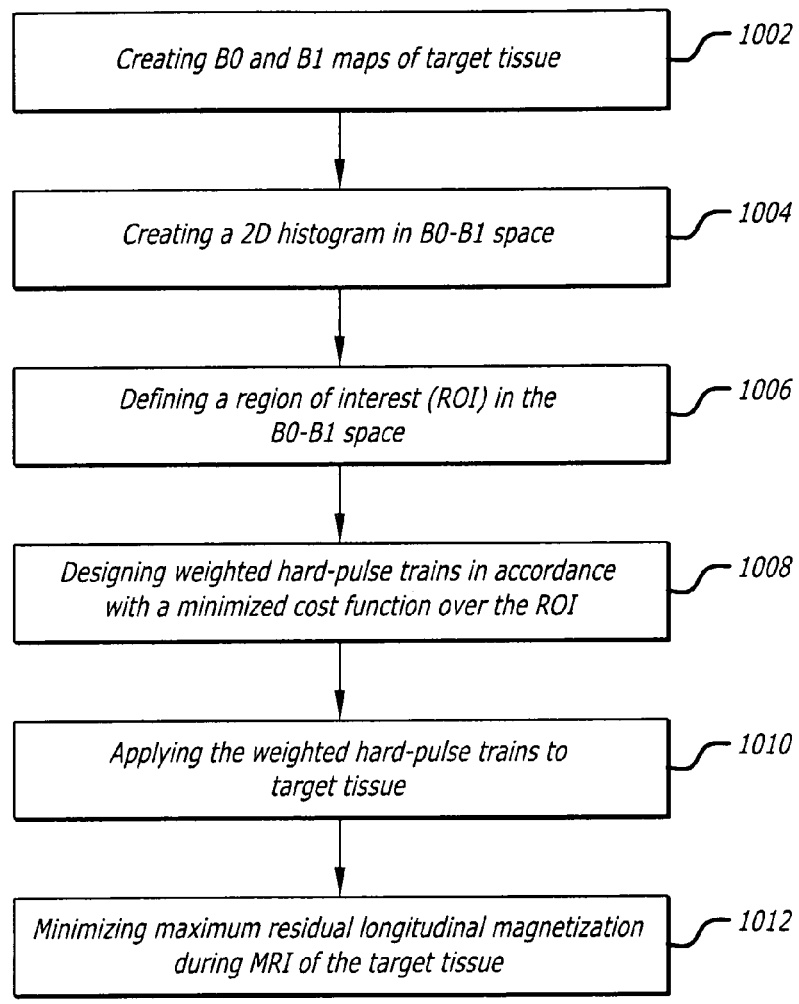

TAILORED RADIOFREQUENCY PULSES FOR UNIFORM SATURATION IN MAGNETIC RESONANCE IMAGING

CROSS-REFERENCE TO RELATED APPLICATION

This application is based upon and claims priority to U.S. Provisional Patent Application No. 61/145,527, entitled "Design of Radiofrequency Pulses for Uniform Saturation in NMR Experiments," filed 14 Nov. 2008, client reference no. 09-164, the entire contents of which are incorporated herein by reference.

BACKGROUND

Complete and uniform saturation of myocardium is essential for quantitative myocardial perfusion imaging using the first pass of a contrast agent. At 3 T, inhomogeneities of both the static (B0) and radiofrequency (B1) magnetic fields have led to the use of adiabatic B1-insensitive rotation type 4 (BIR-4) pulses, which in practice are constrained by radiofrequency (RF) heating.

First-pass magnetic resonance (MR) myocardial perfusion imaging (MPI) is an established technique for the assessment of ischemic heart disease. Saturation recovery preparation is widely used to produce T1-weighted images rapidly and with multiple slice coverage. Contrast-to-noise ratio (CNR) of myocardial wall enhancement during the first pass is critical to the performance of this technique. Recent work at 3 T has demonstrated improved CNR and showed that the diagnostic performance of 3-T MPI is superior to that of 1.5 T for the identification of both single- and multiple-vessel coronary disease. Despite the gain in CNR, there are still major technical challenges in 3-T cardiac imaging, such as static (B0) and radiofrequency (B1) magnetic field inhomogeneities.

Qualitative and quantitative MPI both rely on complete and uniform saturation of myocardium, and the performance of saturation pulses is sensitive to variations in the B0 and B1 fields. Recent studies have compared the effectiveness of different saturation pulses and have shown that the rectangular RF pulse train and the adiabatic B1-insensitive rotation type 4 (BIR-4) pulse exhibit better saturation effectiveness than the conventional 90° rectangular hard pulse with 1.5-T and 3-T cardiac imaging. The conventional RF pulse train, however, is more susceptible to B1 inhomogeneity than the BIR-4 pulse. Conversely, the BIR-4 pulse has a higher specific absorption rate (SAR). These costs inherently limit their application at 3 T, where low RF power deposition and immunity to B0- and B1-field inhomogeneities are highly desirable. At 3 T, inhomogeneities of both the static (B0) and radiofrequency (B1) magnetic fields have led to the use of adiabatic B1-insensitive rotation type 4 (BIR-4) pulses, which in practice are constrained by radiofrequency (RF) heating.

SUMMARY

Embodiments of the present disclosure are directed to systems and methods for providing tailored RF pulse trains, based on estimated B0 and B1 profiles, for uniform saturation for MRI techniques. The tailored pulse trains are optimized to minimize residual longitudinal magnetization in target tissue. The B0 and B1 profiles can be measured a priori over a desired region of a patient, e.g., the heart or abdomen, and can overcome or mitigate SAR and B1 inhomogeneity constraints. In exemplary embodiments, the tailored pulse trains can include hard pulses with unequal weighting. In other embodiments, the tailored pulse trains can include BIR-4 pulse trains that are optimized to minimize residual longitudinal magnetization in target tissue. The tailored pulse train designs can improve the immunity to B1 variation while maintaining low RF power.

An aspect of the present disclosure provides MRI systems for providing tailored pulse trains, based on estimated B0 and B1 profiles, for uniform saturation for MRI techniques.

A further aspect of the present disclosure provides methods for providing tailored pulse trains, based on estimated B0 and B1 profiles, for uniform saturation for MRI techniques.

A further aspect of the present disclosure provides controllers for controlling the production and/or application of tailored pulse trains, based on estimated B0 and B1 profiles, for uniform saturation for MRI techniques.

These, as well as other components, steps, features, objects, benefits, and advantages of the present disclosure, will now become clear from a review of the following detailed description of illustrative embodiments, the accompanying drawings, and the claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

The drawings disclose illustrative embodiments. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it refers to the same or like components or steps.

Figure 1:
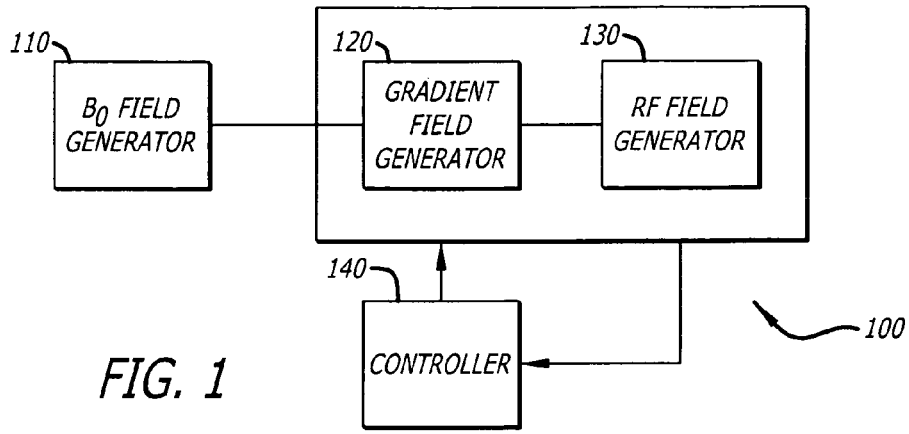
Figure 6:
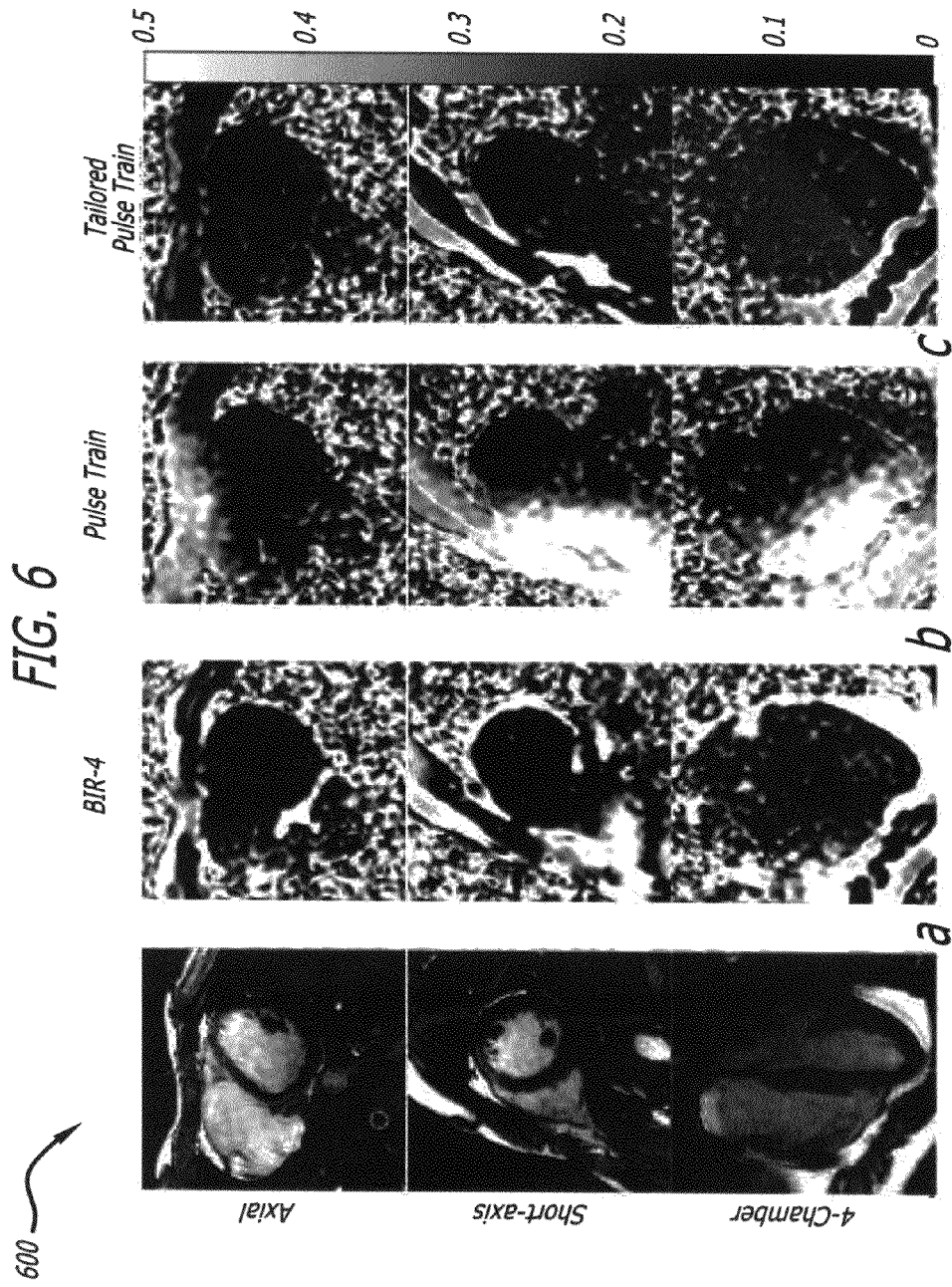
Figure 8A:
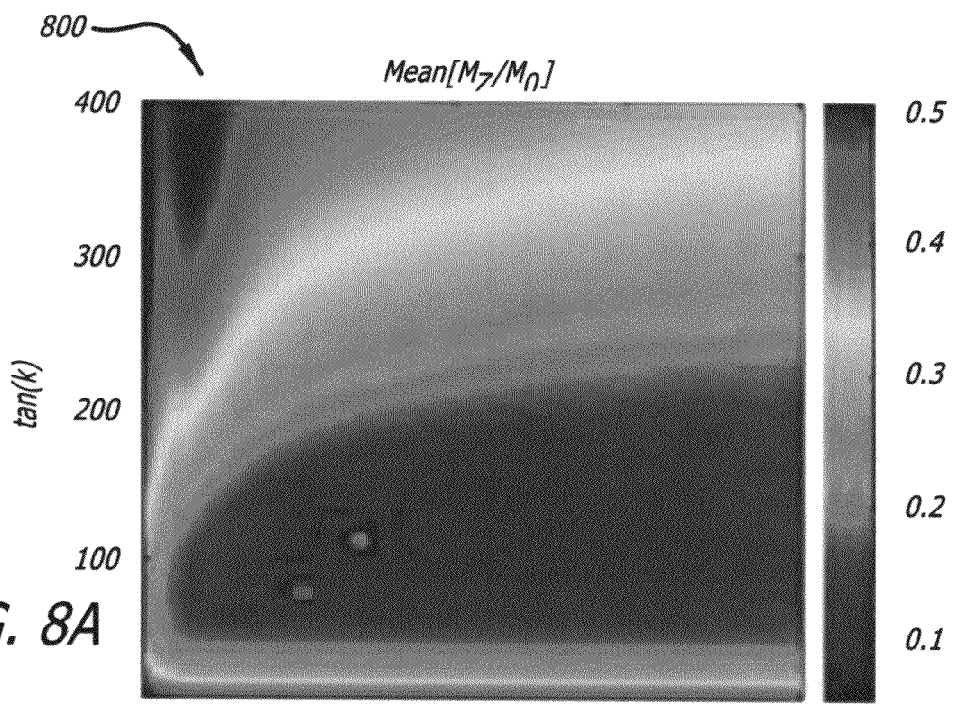
Figure 8B:
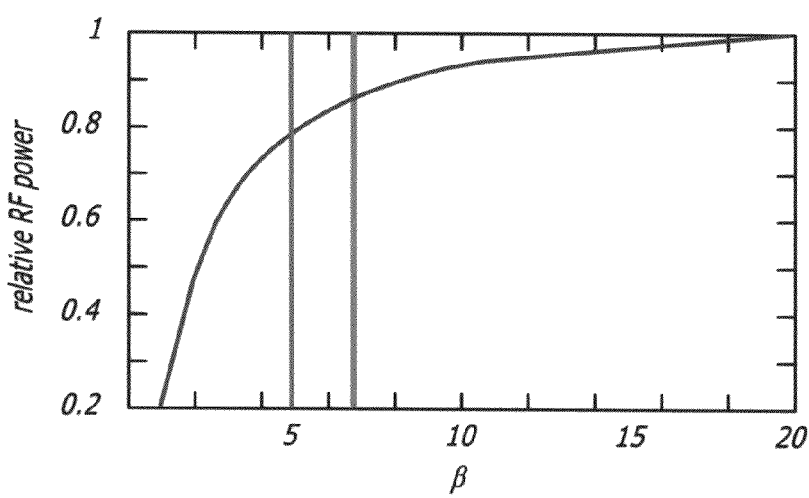

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings:

FIG. 1 depicts a schematic box diagram of a system in accordance with an exemplary embodiment of the present disclosure;

FIG. 2 depicts a set of color measured B0 and B1 maps of inhomogeneity over the left ventricle (LV) at 3 Tesla, and histograms, in accordance with an exemplary embodiment of the present disclosure;

FIG. 3 depicts a table showing prescribed flip angles, Max$|M_z/M_0|$, and relative RF power for optimized tailored pulse trains, in accordance with exemplary embodiments of the present disclosure;

FIG. 4 depicts a set of graphs showing the behavior of residual $M_z$ and the corresponding RF energy as a function of n: (a) Max$|M_z/M_0|$, (b) Mean$|M_z/M_0|$, (c) SD of $M_z/M_0$, and (d) relative RF energy were simulated for the BIR-4 pulse (dotted line), conventional pulse train (gray line), and tailored pulse train (black line), in accordance with an exemplary embodiment of the present disclosure;

FIG. 5 depicts a set of saturation pulse sequence diagrams for three different MRI pulses and a color set of corresponding maximum longitudinal magnetization profiles: (a) the BIR-4, (b) conventional pulse train, and (c) tailored pulse train (n=3), and (d-f) corresponding simulated $|M_z/M_0|$ profiles, in accordance with an exemplary embodiment of the present disclosure;

FIG. 6 depicts a set of representative normalized SR images with (a) the BIR-4, (b) conventional pulse train, and (c) tailored pulse train in three cardiac views, in accordance with an exemplary embodiment of the present disclosure;

FIG. 7 depicts a table showing in vivo performance of myocardial saturation pulses at 3 Tesla, in accordance with an exemplary embodiment of the present disclosure;

FIG. 8 depicts a color plot of optimization of BIR-4 amplitude and frequency modulation function parameters β and tan(κ), in accordance with exemplary embodiments of the present disclosure;

FIG. 9 depicts a set of graphs showing the saturation effectiveness as a function of T1 relaxation times, in accordance with exemplary embodiments of the present disclosure; and FIG. 10 depicts a block diagram of a method designing tailored pulse trains for MRI, in accordance with exemplary embodiments of the present disclosure.

While certain embodiments are depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation. Conversely, some embodiments may be practiced without all of the details that are disclosed.

Embodiments of the present disclosure are directed to systems and methods for providing tailored pulse trains, based on estimated B0 and B1 profiles, for uniform saturation for MRI techniques. The B0 and B1 profiles can be measured a priori over a desired region of a patient, e.g., the heart, and can overcome or mitigate SAR and B1 inhomogeneity constraints. The tailored pulse trains are optimized to minimize residual longitudinal magnetization in target tissue. In exemplary embodiments, the tailored pulse trains can include hard pulses with unequal weighting. In other embodiments, the tailored pulse trains can include BIR-4 pulse trains that are optimized to minimize residual longitudinal magnetization in target tissue. The tailored pulse train designs can improve the immunity to B1 variation while maintaining low RF power. MRI systems, methods, and controllers for providing tailored pulse trains are described.

FIG. 1 illustrates a functional block diagram that provides a schematic overview of an MRI apparatus 100 in accordance with one embodiment of the methods and systems described in the present disclosure. Briefly, the apparatus 100 includes a static field generator 110, a gradient field generator 120, an RF excitation field generator 130, and a controller 140 that controls the operation of the gradient field generator 120 and the RF excitation field generator 130. The controller also analyzes or processes the FID (free induction decay) signals received by a receiver (not shown).

The static field generator 110 generates a strong static magnetic field B0, which is used to line up nuclear spins in a target object (the MRI image of which is being generated by the apparatus 100) along B0. The gradient field generator 120 generates a gradient field G(r), which is superimposed on the static field B0, so that nuclei in a selected plane can be excited by a proper choice of the frequency spectrum of the transverse RF excitation field. The RF excitation field generator 130 generates an RF excitation field B1. When B1 is applied to the object, typically as an RF excitation pulse transverse to B0, the nuclei become excited (due to the RF energy imparted by the RF excitation pulse), so that the nuclear spins rotate by a flip angle. Subsequently, the excited nuclei gradually return to alignment with the static field B0, giving up the excitation energy in the form of weak but detectable FID signals, which are processed by the controller 140 to produce images of the target object. The controller 140 controls the operation of the MRI apparatus 100, including but not limited to the generation of the fields G(r), and B1, as well as the processing of the FID signals resulting from the de-excitation (precession and relaxation) of the nuclei in the object. The RF excitation field generator 130 can be controlled, e.g., by controller 140, to produce a pulse train/sequence of tailored pulses that have been designed to minimize longitudinal magnetization in target tissue, e.g., heart or abdomen, as described in further detail below.

I. Experimental Verification

Experiments were performed to test and validate embodiments of the present disclosure utilizing a commercial whole-body 3.0-T scanner (Signa Excite HD; GE Healthcare, Waukesha, Wis.) with gradients capable of 40-mT/m amplitude and 150-T/m/sec slew rate. A body coil was used for RF transmission and an 8-channel phased-array cardiac coil was used for signal reception. Parallel imaging was not used. In all studies, the transmit gain was calibrated using a standard pre-scan and the center frequency was adjusted over a three-dimensional (3D) region of interest containing the left ventricle (LV). Synchronization with the cardiac cycle was achieved with prospective triggering based on an electrocardiogram (ECG) signal. Each subject was screened for magnetic resonance imaging risk factors and provided informed consent in accordance with institutional policy.

II. Measurement of B0 and B1 Variation

FIG. 2 depicts a set 200 of color measured B0 and B1 maps of inhomogeneity over the left ventricle (LV) at 3 Tesla, and histograms, in accordance with an exemplary embodiment of the present disclosure: (a) B0 and B1 maps from a single slice for one subject, and (b) the combined 2D histogram from all slices for all eight subjects. The extent of the B0-B1 ROI (red rectangle) was based on the extent of the B0-B1 clusters (red oval) computed using Gaussian mixture models for each slice in each subject. The ROI contains 99.7% of all scattered pixels.

The B0 and B1 maps shown in FIG. 2 were measured in 8 healthy subjects (1 female and 7 males, age 29±4.7 years, height 177±5.8 cm, weight 70±7.1 kg) with 6-8 parallel short-axis slices (6 subjects) and 1 short-axis slice (2 subjects). The cardiac B0 maps were obtained in a single breath-hold using cardiac-gated gradient-echo sequences with two echo times (TEs). Signal from fat was reduced using a fat-saturation prepulse. Imaging parameters were: field of view (FOV)=30 cm; in-plane resolution=2.6 mm, TE=1.6 msec and 3.6 msec (±250 Hz frequency range); repetition time (TR)=12.8 ms; flip angle=30°; and slice thickness=5 mm.

With continued reference to FIG. 2, cardiac B1 maps were acquired in a single breath-hold using the cardiac gated saturated double-angle method (SDAM), as previously described, e.g., in Sung K, Nayak K S., *Measurement and characterization of RF nonuniformity over the heart at 3T using body coil transmission*, J. Magn. Reson. Imaging 27:643-648 (2008), the entire contents of which are incorporated herein by reference. The transmit gain was calibrated for each individual subject. The B1 scale was computed as the measured flip angle divided by the prescribed flip angle. Imaging parameters were: FOV=30 cm; in-plane resolution=5 mm; TE=2 msec; TR=7.2 msec; prescribed flip angle=60° and 120°; and slice thickness=5 mm. The LV myocardium was manually segmented in each image, and a composite 2D histogram was produced in B0-B1 space. A region of interest (ROI) was defined that contained B0 and B1 values representative of nearly all myocardial pixels from all subjects and all imaging slices. This ROI was used for subsequent tailored-pulse-train optimization.

Figures 2A, 2B:
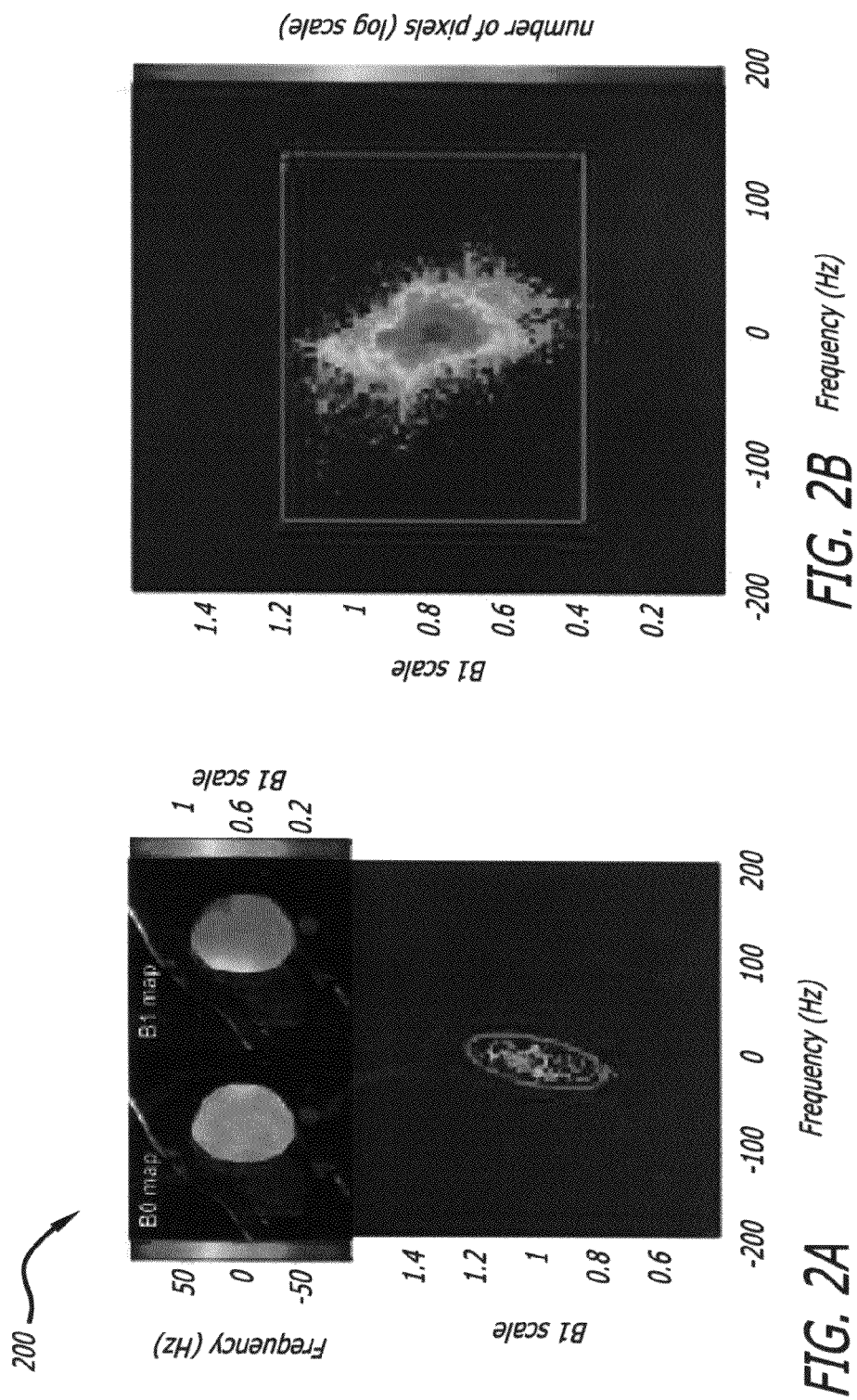
Figure 4A:
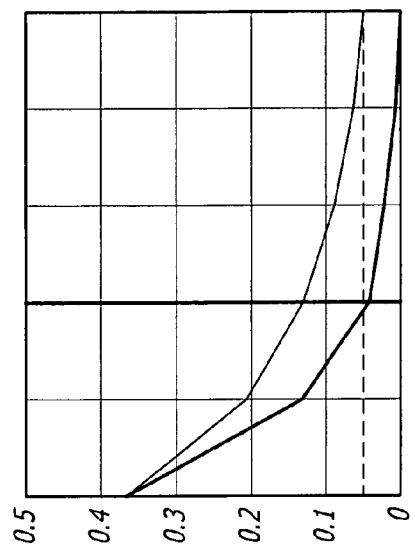
Figure 4B:
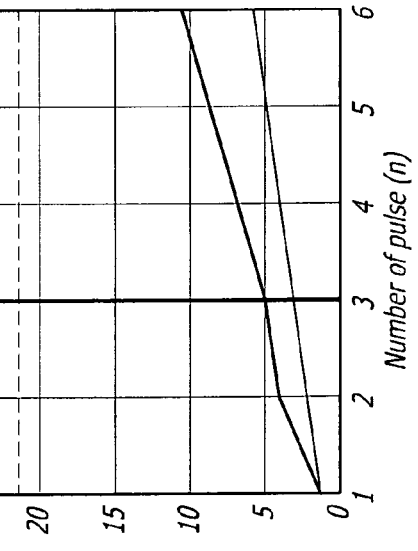
Figure 4C:
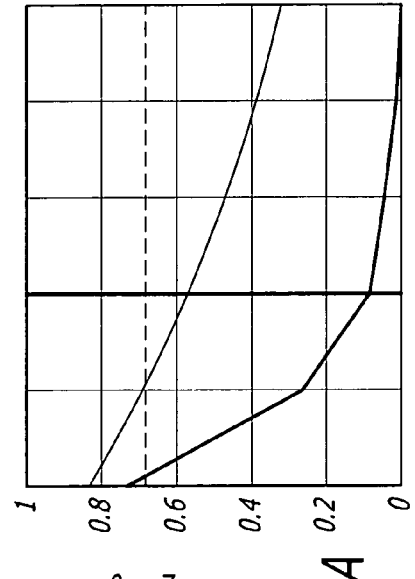
Figure 4D:
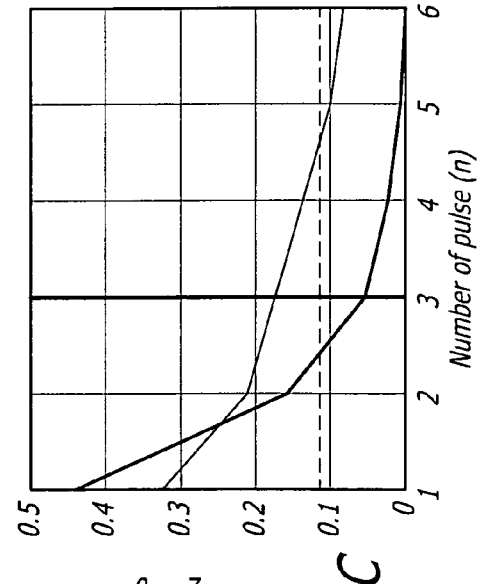

FIG. 2a (top) illustrates the measured B0 and B1 maps from a mid-short-axis slice in one representative volunteer. A Gaussian mixture model (GMM) was initially applied to cluster a region by using the expectation maximization algorithm to estimate the order and parameters of the GMM. For suitable GMM techniques, see, e.g., Everitt B S, Hand D J., *Finite mixture distributions*, Chapman and Hall, (1981), the entire contents of which are incorporated herein by reference. Other clustering techniques may be used in substitution or addition to GMM techniques. The 2D histogram of a given B0-B1 set and its clustered region (red line) are shown in FIG. 2a (bottom).

As shown in FIG. 2b, a rectangular B0-B1 ROI was chosen to represent the expected B0-B1 variation based on the GMM clustered regions, and minimum and maximum B0-B1 values. FIG. 2b shows a 2D histogram of all 8 subjects and its corresponding rectangular ROI, for an exemplary embodiment. The ROI shown overestimates the inhomogeneities of B0-B1 fields to consider all possible cases, and contains 99.7% of all scattered data points. The ROI spans resonance offsets of −144 Hz to +144 Hz, which is in good agreement with the range reported in the literature (see, e.g., Noeske R., et al., *Human cardiac imaging at 3 T using phased array coils*, Magn. Reson. Med., 44:978-982 (2004), the entire contents of which are incorporated herein by reference), and a B1 scaling range of 0.38-1.2, which contains the range obtained in a previous study (0.45-1.12), i.e., Sung K, Nayak K. S., *Measurement and characterization of RF nonuniformity over the heart at 3 T using body coil transmission*, J. Magn. Reson. Imaging, 27:643-648 (2008).

III. Optimization of Pulse Trains

Based on the B0-B1 ROI of FIG. 2b, weighted hard-pulse trains $(\alpha_1, \ldots, \alpha_n)$ of length n were designed to minimize the maximum residual longitudinal magnetization (Mz) over the B0-B1 ROI. For the optimization, an exhaustive search based on numerical Bloch simulations was performed with the following cost function:

$$c = \max_{ROI} \left| \frac{M_z}{M_0} \right| \quad \text{(EQ. 1)}$$

The pulse train weighting of an exemplary embodiment was optimized to produce the minimum cost according to EQ. 1, as shown in FIG. 3.

FIG. 3 depicts Table 1 (reference character 300) which contains the optimal flip angles for n=1-6, and the corresponding max |Mz/M0| and relative RF energies, in accordance with exemplary embodiments of the present disclosure. The relative RF energy was calculated as the RF energy of a pulse train divided by the RF energy of a single 90° hard pulse (duration 0.5 msec).

For the optimization, each $\alpha_i$ ranged from 70° to 240° in steps of 1° for n≦3, and 5° for otherwise (4≦n≦6). Minimum and maximum $\alpha_i$ constraints were determined by 90° divided by the minimum and maximum B1 scale of the ROI. Other maxima determination techniques can of course be utilized. The peak B1 amplitude was fixed at 0.115 G, a typical value of body-coil transmission in commercial scanners when imaging medium to large-sized humans. T1 relaxation between RF subpulses was ignored, and the residual transverse magnetization was assumed to be completely removed by the crusher gradients. Therefore, the subpulses in a set $(\alpha_1, \ldots, \alpha_n)$ had no specific order, reducing the computation time.

IV. Exemplary Embodiments

Simulated Pulse Performance

FIG. 4 depicts a set 400 of four plots (a-d) showing the residual Mz/M0 and the RF energy as a function of n in simulation, for embodiments designed in accordance with the weighting shown in FIG. 3. The maximum values of |Mz/M0| within the ROI for the tailored pulse train were compared with those for the BIR-4 and pulse train. Because the rectangular ROI was selected to overestimate the actual behavior of B0-B1 inhomogeneity for each subject, the average |Mz/M0| value was computed and also the standard deviation (SD) of Mz/M0 over the ROI. The tailored-pulsetrain designs showed superior saturation performance compared with the conventional pulse train, with only a small increment in the relative RF energy. When n=3, the behavior of the residual Mz/M0 (max |Mz/M0|, mean |Mz/M0|, and SD Mz/M0) for the tailored pulse train indicated better saturation performance compared with the BIR-4 pulse, while maintaining lower relative RF energy.

FIG. 5 includes views (a-f) and depicts a set 500 of saturation pulse sequence diagrams for three different MRI pulses and a color set of corresponding maximum longitudinal magnetization profiles, in accordance with an exemplary embodiment of the present disclosure.

FIGS. 5a-c shows pulse sequence diagrams for the three different saturation pulses considered: (a) the BIR-4, (b) conventional pulse train, and (c) a tailored pulse train (n=3) of an exemplary embodiment. The tailored pulse train (n=3) had a 7.7-msec pulse duration (FIG. 5c). The optimal pulse weighting was 96°, 228°, and 141° (0.548, 1.296, and 0.804 msec, respectively), and the order was chosen among all the six possible combinations by including T1 relaxation (T1=1115 msec) in the cost function. The spoiler gradients (1 ms) and crusher gradients (3 msec-2 msec-2 msec) were cycled to avoid stimulated echoes. The tailored pulse train of the embodiment was seen to produce 4.2 times lower relative RF energy than the BIR-4 pulse, and 1.7 times higher relative RF energy than the pulse train.

FIGS. 5d-f shows the saturation profiles as a function of off-resonance (horizontal axis) and B1 scale (vertical axis) using numerical Bloch simulation for the three saturation pulses depicted in FIGS. 5a-c. The ROI used for optimization is shown in red. The profile for the BIR-4 pulse (FIG. 5d) was shown to have excellent saturation for most of the B1 range, but its B0 bandwidth became less than ±110 Hz as the B1 scale fell below 0.43. This may potentially be problematic when both the B0 and B1 fields are severely distorted. The conventional pulse train (FIG. 5e) showed excellent B0 variation insensitivity due to its effective bandwidth of ±1000 Hz, but the peak Mz/M0 became larger than 0.1 when the B1 scale was smaller than 0.7. This may explain the weaker B1 immunity of the pulse train, as previously discussed. The tailored pulse train with the optimal weighting (FIG. 5f), however, improved the saturation performance, and produced excellent saturation effectiveness over the entire ROI.

V. Exemplary Embodiments

In Vivo Pulse Performance

In vivo tests of exemplary embodiments of tailored pulses were performed in four healthy volunteers (one female and three males, age 31±2.1 years, height 173±5.3 cm, weight 67±8.1 kg) with three cardiac views (axial, short-axis, and four-chamber).

FIG. 6 shows a set 600 of representative normalized SR images with the different saturation pulses (a-c) in three cardiac views obtained from the in vivo tests. Cardiac cine images (left column) are displayed to provide an anatomical reference. Table 2 shown in FIG. 7 summarizes the saturation effectiveness for the different saturation pulses of FIG. 6.

The tailored pulse train with n=3 was compared with an 8-ms BIR-4 pulse with tanh/tan (amplitude/frequency) modulation functions, $\beta=5$ and $\tan(\kappa)=80$, (e.g., as described in Staewen R. S. et al., *3-D FLASH imaging using a single surface coil and a new adiabatic pulse, BIR-4*, Invest Radiol 1990; 25:559-56, the entire contents of which are incorporated herein by reference), and conventional pulse train using a saturation-no-recovery (SR) experiment, as previously described, see, e.g., Kim D., et al., *B(0) and B(1)-insensitive uniform T(1)-weighting for quantitative, first-pass myocardial perfusion magnetic resonance imaging*, Magn. Reson. Med. 54:1423-1429 (2005); and Kim D., et al., *Comparison of the effectiveness of saturation pulses in the heart at 3 T*, Magn. Reson. Med., 59:209-215 (2008). Identical transmit gain and shim values were maintained during the comparison. A 2DFT fast gradient echo (FGRE) acquisition with a center-out k-space trajectory was used with a 10° flip angle. Proton-density (PD) weighted images with a 3° flip angle were also acquired in the same breath-hold for normalization. The pulse sequence was cardiac-gated and there was one heartbeat between SR and PD acquisition to allow full recovery of magnetization, resulting in a single breath-hold of 5 heartbeats (2 for SR images, 1 for recovery, and 2 for PD images). Each saturation pulse (BIR-4, pulse train, and tailored pulse train) was employed in the FGRE pulse sequence, and acquired in a separate breath-hold. Imaging parameters were: FOV=30 cm; TE=1.2 msec; TR=3.4 msec, acquisition matrix=64×64; in-plane resolution=4.7 mm; slice thickness=5 mm; image acquisition time=109 msec; and bandwidth±125 kHz.

For image analysis, the SR images were normalized by the PD images (SR/PD) to remove the effect of receive coil sensitivity and other system imperfections, and then multiplied by sin 3°/sin 10° to compensate for the excitation angle difference. The resulting images show |Mz/M0| and have a range from 0 (complete saturation) to 1 (no saturation). LV and right ventricle (RV) were manually defined based on the PD images. The maximum and average |Mz/M0| over the LV and LV+RV were computed, and report mean±SD. All image analysis and numerical simulations were performed in MATLAB, version 7.0 (The Mathworks, Inc., Natick, Mass.). Other suitable software may of course be used to obtain desired analysis and simulation.

With continued reference to FIGS. 6-7, both the BIR-4 and tailored pulse showed comparable saturation performance over the LV, whereas the conventional pulse train became less effective in septal myocardium. The peak and average residual |Mz/M0| over the LV for the tailored pulse train were smaller than those for the BIR-4 and conventional pulse train, but only the peak value was significantly different (P<0.05). The residual |Mz/M0| within the LV+RV behaved differently, and the BIR-4 pulse demonstrated inferior performance compared with the tailored pulse train. The peak and average residual |Mz/M0| over the LV+RV for the tailored pulse train were significantly smaller than those for the BIR-4 and conventional pulse train (P<0.05). Note that the measured values were influenced by low SNR and T1 recovery during the acquisition, and therefore could not represent the absolute saturation effectiveness.

VI. Analysis of Exemplary Embodiments

Embodiments of tailored RF pulse trains were implemented both in simulation and in vivo and were shown to increase immunity to B0 and B1 variation. It was demonstrated (e.g., as shown in FIG. 6) that trains of tailored hard RF pulses had superior saturation effectiveness in simulation and in vivo, with the cost of 1.7-times-higher RF power than the conventional 90° pulse train for exemplary embodiments. Compared with the BIR-4 pulse, the tailored pulses of in vivo and simulation embodiments showed superior saturation over the heart while requiring 4.2 times less RF power. Thus, embodiments of tailored pulses according to the present disclosure can alleviate or mitigate the SAR constraints and can enable more frequent use of saturation pulses or more extensive coverage in target tissue, e.g., of the myocardium in 3-T MPI (e.g., more slices per heartbeat).

The total number of subpulses were confined to three in exemplary embodiments validated, because three subpulses were the minimum number that was predicted to produce saturation performance superior to both the conventional pulse train and BIR-4. Of course, more or fewer pulses can be utilized. Tailored pulse trains with more than three subpulses may improve the saturation performance (max |Mz/M0| and mean |Mz/M0|) with a small increment in RF power and pulse duration, as shown in Table 1 of FIG. 3. It should be noted that BIR-4 pulses can also be optimized based on B0-B1 maps—for example, when choosing amplitude and frequency modulation functions.

FIG. 8 shows the mean|Mz/M0| as a function of $\beta$, the amplitude modulation function parameter, and $\tanh(\kappa)$, the frequency modulation function parameter, with a fixed RF pulse duration (8 msec). As shown, an optimized BIR-4 pulse can reduce average residual Mz by 4.3% while increasing RF power by 8.3%.

VII. Additional Considerations

Paramagnetic contrast agents during the first pass, and stents, sternal wire, and other metal implants can potentially create additional B0 inhomogeneity due to increased susceptibility effects, widening the B0-B1 ROI. Embodiments of the present disclosure include tailored pulse trains including RF pulses with different bandwidths, e.g., that may have an effective B0 bandwidth of ±390 Hz, etc. Therefore, the additional off-resonance caused by the contrast agents is not expected to degrade the saturation performance of embodiments having tailored pulse trains with hard pulses. The saturation performance of the BIR-4 pulse embodiments, due to more limited bandwidth, can be impacted. The effective bandwidth in the tailored hard-pulse train embodiments can be increased by either lowering the maximum $\alpha_i$ constraint in the cost function or increasing the peak B1 amplitude in the pulse design.

First-pass contrast agents also cause a reduction in T1 relaxation time, and longitudinal recovery during saturation may affect pulse performance, e.g., as depicted in FIG. 9.

FIG. 9 depicts a set 900 of graphs (a)-(c) showing the results of a numerical simulation of the residual |Mz/M0| within the ROI with different T1 relaxation times (50-2000 msec). The BIR-4 pulse showed the least T1 dependency with <2% variation for all cases (max |Mz/M0|, mean |Mz/M0|, and SD Mz/M0), but the tailored pulse train also maintained comparable saturation performance in the short T1 regime. Based on the robustness to off-resonance and T1 dependency, saturation pulses according to the present disclosure may be expected to maintain performance under the conditions of dynamic contrast-enhanced MRI. For tested embodiments, e.g., shown and described for FIG. 2, the B1 scale range in the ROI (0.38-1.2) overestimated the actual B1 behavior of each subject because the individual B1 distribution never spanned the entire B1 scale range. This can be partially attributed to errors in the transmit gain calibration and, specifically, the fact that transmit gain is typically calibrated based on a signal from an entire slice or prescribed volume. Similar to localized shimming and localized center frequency adjustment, the localized calibration of the transmit gain specifically to the heart (or other target region) would be desirable to produce a more accurate and tighter expected B1 scale range.

FIG. 10 depicts a block diagram of a method 1000 of designing tailored pulse trains for MRI, in accordance with exemplary embodiments of the present disclosure. B0 and B1 maps can be created, e.g., measured from one or more subjects, as described at 1002. Exemplary embodiments can use MRI techniques useful for cardiac imaging such as cardiac-gated gradient-echo sequences with two echo times for M0 maps and cardiac-gated saturated double-angle methods (SDAM) for B1 maps. Signal from lipid can be reduced using a lipid (fat) saturation prepulse if desired. Transmit gain for each individual subject can be calibrated. A B1 scale can be computed as the measured flip angle divided by the prescribed flip angle.

A histogram of can be created in B0-B1 space, e.g., a composite 2D histogram, as described at 1004. As described at 1006, a region of interest (ROI) can be defined, e.g., one that contains all or nearly all of the B0 and B1 values representative of myocardial (or other tissue) values from some (including an individual alone) or all subjects and some or all imaging slices. The ROI can be used for subsequent pulse train optimization.

Continuing with the description of method 1000 of FIG. 10, weighted hard pulse trains can be designed or tailored in accordance with a minimized cost function, e.g., EQ. 1, that seeks to minimize maximum residual longitudinal magnetization ($M_z$) over the ROI, as described at 1008. In other embodiments, B1-independent rotation pulses, e.g., BIR-4 pulses, can be optimized by based on B0-B1 maps and/or a ROI, for example by seeking to minimize residual magnetization $$\left(\mathrm{mean}\left|\frac{M_z}{M_0}\right|\right).$$

The tailored pulse trains so designed can be applied to target tissue, e.g., a LV, as described at 1010. As a result, maximum residual longitudinal magnetization can be minimized for MRI of the target tissue, as described at 1012. BIR-4 amplitude and frequency modulation parameters are described in Staewen R. S., et al., 3-D FLASH imaging using a single surface coil and a new adiabatic pulse, BIR-4. Invest. Radiol., 25:559-567 (1990), the entire contents of which are incorporated herein by reference.

Accordingly, embodiments of the present disclosure can provide for the design and utilization of tailored RF pulse trains, which can overcome or mitigate SAR and/or B1 inhomogeneity constraints for MRI. Exemplary embodiments of the tailored pulse trains are optimized to minimize residual longitudinal magnetization and can include hard pulses with unequal weighting (or different combinations of flip angles). Other embodiments can include BIR-4 pulse trains/waveforms. The tailored pulse-train design can improve the immunity to B1 variation, while maintaining low RF power. Embodiments of the present disclosure can facilitate accurate T1 weighting. Embodiments of the use of tailored pulse trains have been described and experimentally validated that optimally saturate myocardium at 3 T, based on measurements of typical B0 and B1 field variation. Weighted hard pulse trains according to the present disclosure are simple to design, require substantially lower RF power compared with BIR-4 pulses, and show higher B1 insensitivity compared with conventional hard pulse trains. Furthermore, the proposed saturation pulse demonstrated lower peak and average residual $M_z/M_0$ over the heart at 3 T, compared with a standard 8-msec BIR-4 pulse and a conventional hard pulse train ($P \leq 0.05$). Tailored pulse trains may therefore have an important beneficial role in quantitative first-pass myocardial perfusion imaging, e.g., at 3 T or other field strengths.

Examples of applications of embodiments of the present disclosure can include, but are not limited to, first-pass myocardial perfusion imaging, saturation recovery based B1 mapping, saturation recovery based T1 mapping, fat saturation, and T1-weighted abdominal imaging. In application and for different MRI scanner configurations, e.g., 1.5 T scanners v. 3 T scanners, the optimum combination of flip angles can be different, since possible B0 and B1 field inhomogeneities can be different for different applications and setups. Accordingly, the values of Table 1 (FIG. 3) may be optimal for cardiac applications but not necessarily for other applications. In addition, the optimum number of subpulses can be different for different pulse sequences since each pulse sequence can be limited by different RF power constraints. As described previously, embodiments of tailored pulse sequences/designs according to the present disclosure can also be applied to other areas of the body such as the abdomen. Tailored pulse trains can be optimized with respect to the B0-B1 ROI of each application, which in the abdomen could include fat/lipid.

The components, steps, features, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits and advantages. These also include embodiments in which the components and/or steps are arranged and/or ordered differently.

In reading the present disclosure, one skilled in the art will appreciate that embodiments of the present disclosure can be implemented in hardware, software, firmware, or any combinations of such, and over one or more networks. Suitable software can include computer-readable or machine-readable instructions for performing methods and techniques (and portions thereof) of designing and/or controlling the implementation of tailored RF pulse trains. Any suitable software language (machine-dependent or machine-independent) may be utilized. Moreover, embodiments of the present disclosure can be included in or carried by various signals, e.g., as transmitted over a wireless RF or IR communications link or downloaded from the Internet.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials that have been described and their equivalents. Similarly, the phrase "step for" when used in a claim embraces the corresponding acts that have been described and their equivalents. The absence of these phrases means that the claim is not intended to and should not be interpreted to be limited to any of the corresponding structures, materials, or acts or to their equivalents.

Nothing that has been stated or illustrated is intended or should be interpreted to cause a dedication of any component, step, feature, object, benefit, advantage, or equivalent to the public, regardless of whether it is recited in the claims.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

What is claimed is:

1. A method of uniform-saturation magnetic resonance imaging, the method comprising:
   with a MRI system, creating B0 and B1 maps of target tissue;
   creating a 2D histogram in B0-B1 space;
   defining a region of interest (ROI) in the B0-B1 space;
   designing an optimized weighted hard-pulse train that minimizes maximum residual longitudinal magnetization over the ROI during MRI of the target tissue; and
   with a RF excitation field generator, applying the optimized weighted hard-pulse train to the target tissue.

2. The method of claim 1, wherein designing an optimized pulse rain comprises designing a weighted hard-pulse train in accordance with a minimized cost function over the ROI.

3. The method of claim 2, wherein the cost function is expressed in the form, $$C = \max_{ROI} \left| \frac{M_z}{M_0} \right|$$

wherein $M_z$ is the longitudinal magnetization and $M_0$ is the net magnetization in the direction of protons aligned along the external magnetic field, respectively.

4. The method of claim 2, further comprising reducing signals from lipids by applying a lipid-saturation prepulse.

5. The method of claim 2, further comprising providing a plurality of phase encoding steps, wherein each phase encoding step comprises a slice selection gradient, a phase encoding gradient, and a readout gradient.

6. The method of claim 2, wherein the weighted hard-pulse train comprises a pulse (N=1) with a flip angle of about 114°.

7. The method of claim 2, wherein the weighted hard-pulse train comprises two pulses (N=2) with flip angles of about 116° and about 231°, respectively.

8. The method of claim 2, wherein the weighted hard-pulse train comprises three pulses (N=3) with flip angles of about 96°, about 228°, and about 141°, respectively.

9. The method of claim 2, wherein the weighted hard-pulse train comprises four pulses (N=4) with flip angles of about 120°, about 90°, about 180°, and about 230°, respectively.

10. The method of claim 2, wherein the weighted hard-pulse train comprises five pulses (N=5) with flip angles of about 90°, about 110°, about 145°, about 205°, and about 235°, respectively.

11. The method of claim 2, wherein the weighted hard-pulse train comprises six pulses (N=6) with flip angles of about 90°, about 170°, about 130°, about 105°, about 220°, and about 240°, respectively.

12. The method of claim 1, wherein designing an optimized pulse train over the ROI comprises using the B0-B1 maps for choosing frequency and modulation functions for a BIR-4 pulse train.

13. The method of claim 12, wherein designing an optimized pulse train comprises minimizing residual magnetization over the ROI.

14. The method of claim 1, wherein creating a 2D histogram in B0-B1 space comprises using a Gaussian mixture model (GMM) to cluster a region in B0-B1 space.

15. A MRI system for generating MRI images of an object, the MRI system comprising:
   a static field generator configured to generate a static magnetic field B0;
   a gradient field generator configured to generate a time-varying gradient field G(r), parallel to B0; and
   a RF excitation pulse generator configured to generate a RF excitation field B1 and apply the field B1 to the object so that nuclear spins in the object flip at a flip angle, wherein the RF excitation field comprises a tailored pulse sequence of RF and gradient pulses; and
   a processing system configured and arranged to apply weighting for the tailored pulse sequence based on a region of interest (ROI) inside of target tissue, wherein the processing system is configured and arranged to apply weighting for the tailored pulse sequence in accordance with a minimized cost function over the ROI.

16. The system of claim 15, wherein the processing system comprises an image processing system.

17. The system of claim 15, wherein the cost function is expressed in the form, $$C = \max_{ROI} \left| \frac{M_z}{M_0} \right|$$

wherein Mz is the longitudinal magnetization and Mo is the net magnetization in the direction of protons aligned along the external magnetic field, respectively.

18. The system of claim 15, wherein the tailored pulse sequence comprises a weighted hard-pulse train including a pulse (N=1) with a flip angle of about 114°.

19. The system of claim 15, wherein the tailored pulse sequence comprises a weighted hard-pulse train including two pulses (N=2) with flip angles of about 116° and about 231°, respectively.

20. The system of claim 15, wherein the tailored pulse sequence comprises a weighted hard-pulse train including three pulses (N=3) with flip angles of about 96°, about 228°, and about 141°, respectively.

21. The system of claim 15, wherein the tailored pulse sequence comprises a weighted hard-pulse train including four pulses (N=4) with flip angles of about 120°, about 90°, about 180°, and about 230°, respectively.

22. The system of claim 15, wherein the tailored pulse sequence comprises a weighted hard-pulse train including five pulses (N=5) with flip angles of about 90°, about 110°, about 145°, about 205°, and about 235°, respectively.

23. The system of claim 15, wherein the tailored pulse sequence comprises a weighted hard-pulse train including six pulses (N=6) with flip angles of about 90°, about 170°, about 130°, about 105°, about 220°, and about 240°, respectively.

24. The system of claim 15, wherein the tailored pulse sequence comprises a BIR-4 pulse train.

25. The system of claim 24, wherein the BIR-4 pulse trains comprise an optimized pulse train having minimized residual magnetization over the ROI.

26. The system of claim 25, wherein the BIR-4 pulse train has a $\beta$ of about 6.8 and $\tanh(\kappa)$ of about 112, wherein $\beta$ is the amplitude modulation function parameter and $\tanh(\kappa)$ is the frequency modulation function parameter.

* * * * *